United States Patent [19]
Anderson

[11] Patent Number: 5,893,365
[45] Date of Patent: Apr. 13, 1999

[54] APPLIANCE FOR PREVENTING SNORING AND OBSTRUCTIVE SLEEP APNEA

[76] Inventor: Clarence D. Anderson, 6526 E. Holly Dr., Mesa, Ariz. 85215

[21] Appl. No.: 08/901,703

[22] Filed: Jul. 28, 1997

[51] Int. Cl.$^6$ .................................................. A61F 5/56
[52] U.S. Cl. .................. 128/848; 128/857; 128/859; 602/17; 602/902
[58] Field of Search .................. 128/848, 857–862; 602/16, 17, 902; 2/2

[56] References Cited

U.S. PATENT DOCUMENTS

| | | | |
|---|---|---|---|
| 649,896 | 5/1900 | Baughman | 128/848 |
| 678,417 | 7/1901 | Muller | 602/17 |
| 1,629,892 | 5/1927 | Storms | 128/848 |
| 2,304,235 | 12/1942 | Boots | 128/848 |
| 4,169,473 | 10/1979 | Samelson . | |
| 4,304,227 | 12/1981 | Samelson . | |
| 4,366,815 | 1/1983 | Broomes . | |
| 5,056,534 | 10/1991 | Wright . | |
| 5,117,816 | 6/1992 | Shapiro et al. . | |
| 5,277,202 | 1/1994 | Hays . | |
| 5,313,960 | 5/1994 | Tomasi . | |
| 5,316,020 | 5/1994 | Truffer . | |
| 5,365,945 | 11/1994 | Halstrom . | |
| 5,373,859 | 12/1994 | Forney . | |
| 5,427,117 | 6/1995 | Thornton . | |
| 5,462,066 | 10/1995 | Snyder . | |
| 5,465,734 | 11/1995 | Alvarez . | |
| 5,467,783 | 11/1995 | Meade . | |
| 5,499,633 | 3/1996 | Fenton . | |

*Primary Examiner*—Michael A. Brown
*Attorney, Agent, or Firm*—John D. Lister

[57] ABSTRACT

An appliance for preventing snoring and sleep apnea includes a headgear and a mouthpiece. The headgear includes an adjustable headband encircling the upper portion of a user's head at the forehead; an adjustable chin strap passing over the crown of the head and under the chin of the user to maintain the user's mouth closed about the mouthpiece; a back strap passing from the forehead over the crown of the head and down the back of the user; a means secured to the rear end of the back strap for exerting a restraining force on the back strap and the upper portion of the headgear to keep the user's head from slouching forward; and an object secured to the rear end of the back strap for making it uncomfortable for the user to lie on his/her back. The mouthpiece includes a thin, flexible front sheet extending across the front of the user's mouth in front of the user's teeth to prevent breathing through the mouth and a thin, flexible back tab extending from an inner upper portion of the flexible sheet to behind the user's lower front teeth for pulling the user's lower jaw forward.

14 Claims, 3 Drawing Sheets

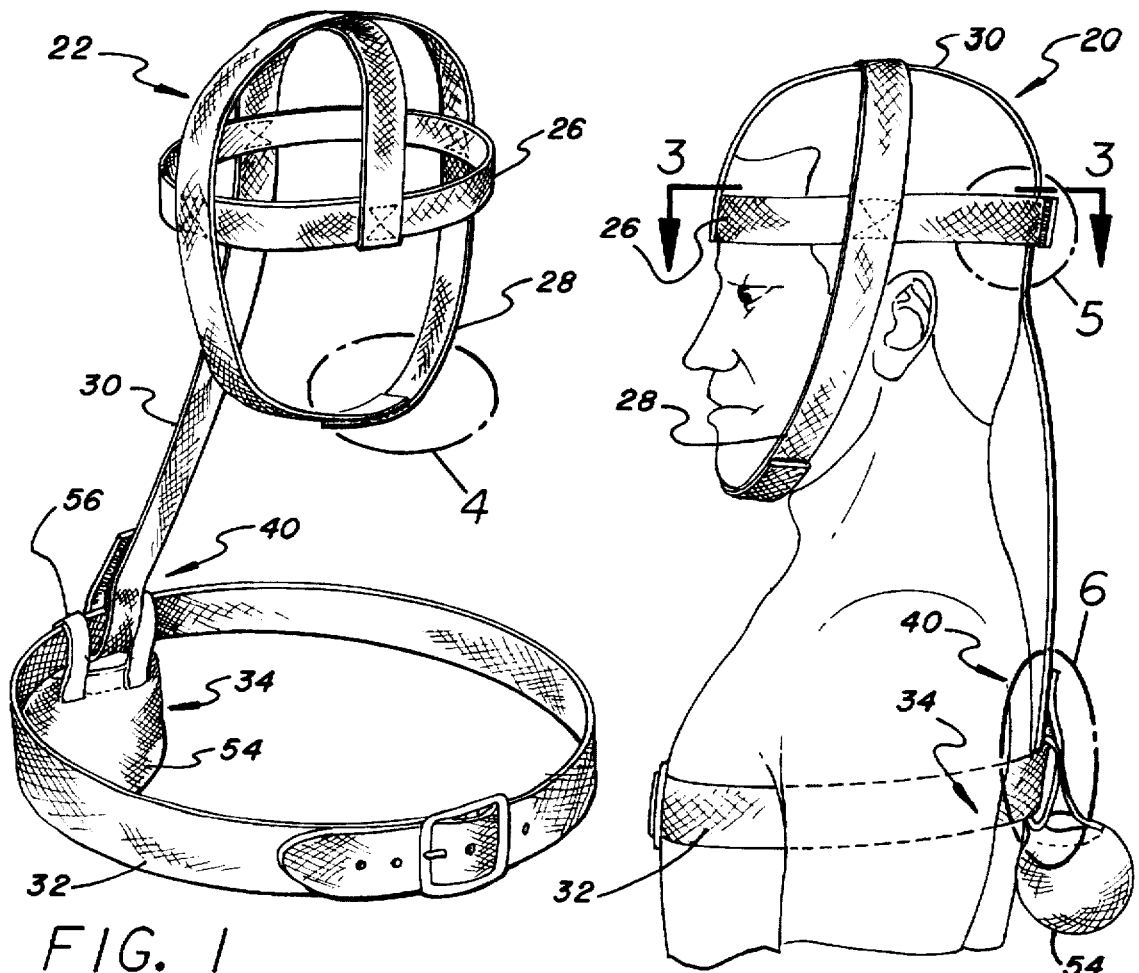
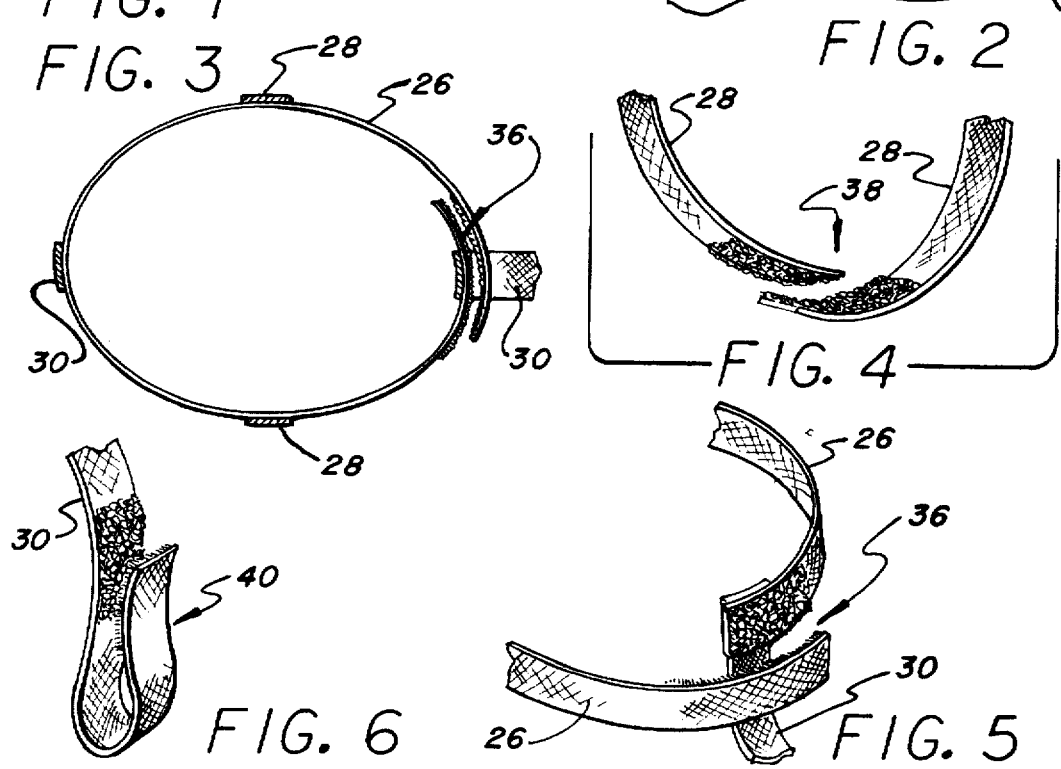

APPLIANCE FOR PREVENTING SNORING AND OBSTRUCTIVE SLEEP APNEA

BACKGROUND OF THE INVENTION

The present invention relates to an appliance for preventing snoring and obstructive sleep apnea, and in particular, to an appliance which utilizes a headgear and mouthpiece that function as a unit to provide the necessary relief from snoring and obstructive sleep apnea.

As discussed in U.S. Pat. No. 4,551,473, one of the most misunderstood ailments of man is the noisy breathing pattern that occurs in some persons during sleep. Afflicted persons may create so much sonic disturbance that they prevent sleep in bed partners, roommates, and sometimes persons several rooms distant. Throughout history snorers have been ridiculed, harassed and subjected to mounting hostility of other household members. As might be expected, an almost endless variety of well meaning or defensive attempts have been made to control snoring. Most such devices function by subjecting the unfortunate person to unpleasant mechanical or electrical stimuli as soon as snoring commences and are successful only to the degree that the snorer is kept from sleeping.

As has been pointed out a paper by David N. F. Fairbanks, M.D. ("Snoring: Not Funny-Not Hopeless", HOSPITAL MEDICINE, March, 1984), the noise of snoring comes from vibrations of soft tissues in the collapsible part of the upper airway, involving the soft palate, uvula, tonsils and tonsillar pillars, base of the tongue, and pharyngeal muscles and mucosa. Other medical literature expresses the opinion that, for most persons, snoring is caused by muscle relaxation that occurs during sleep. It is postulated that, as the muscles of the mouth, nose, and throat relax, the negative pressure that occurs during inspiration encourages the tongue to fall backward into the airway and vibrate against a relaxed and floppy soft palate and uvula. At the same time, the lateral pharyngeal structures are drawn inward, further constricting the airway and increasing the speed of air flow pat the vibrating structures.

The following conditions have been found to increase the problem of snoring and obstructive sleep apnea. Obesity further constricts the airway, increases the work of breathing and further compounds the problem. Temporary swelling caused by hay fever, inflamed sinuses, etc. also narrow the air passages and cause snoring in a person normally free from that affliction. However, the use of antihistamines promotes drying of the mucous membranes and further promotes vibration in the relaxed structures. Smoking, two byproducts of which are carbon monoxide and formaldehyde, tends to stimulate snoring by drying or irritating the air passages, inducing hypoxemia, and even causing the swallowing muscles to spasm. When an afflicted person uses central nervous system depressants, such as alcoholic beverages or tranquilizers before retiring, it has been found that the tendency to snore is exacerbated.

As socially unattractive as snoring may be, sleep apnea, which frequently accompanies snoring, is much more dangerous. In some cases, the relaxed tissues of the airway may so effectively seal off the passage of air to the lungs as to completely prevent inspiration. Persons suffering from this problem may actually stop breathing 30 to 300 times per night for periods of ten seconds to two minutes (three minutes may be fatal). Consequently, such persons spend as much half of their sleep time with abnormally low blood oxygen levels. Such persons resume normal breathing, albeit briefly, when they wake into a lighter sleep stage, causing the relaxed muscles to tense sufficiently to relieve the obstruction. As will be appreciated, persons with obstructive sleep apnea spend an insufficient portion of their nighttime hours in the deep sleep stages that are essential for good rest, awakening unrefreshed and feeling sleepy much of the day. In addition to the above, cardiac arrhythmias may occur during apneic episodes that can possibly lead to death in sleep.

One method of curing the related problems of snoring and obstructive sleep apnea has been the surgical removal of what has been considered excess tissue in the air passageway by means of palatopharyngoplasty. Although effective in many instances, the operation is painful, expensive, and fraught with the dangers accompanying any operation in the blood rich throat area. Other attempts to cure the problems of snoring and obstructive sleep apnea have involved the use of medications, such as the muscle relaxants referred to in U.S. Pat. No. 4,551,473. Other methods of treating snoring and/or sleep apnea have involved the use of mouthpieces, such as the mouthpieces of U.S. Pat. Nos. 4,169,473; 4,304,227; 5,506,534; 5,117,816; 5,277,202; 5,313,960; 5,316,020; 5,365,945; 5,373,859; 5,427,117; 5,462,066; 5,465,734; 5,467,783; and 5,499,633.

In addition to the other methods for treating snoring and obstructive sleep apnea discussed above, constant, positive air pressure machines (CPAP machines) are sometimes used to treat snoring and obstructive sleep apnea by providing constant positive air pressure to the nostrils. The machine includes a hose, leading from a fan, to a headgear that holds the hose outlet near the nose. The nose is either covered with a mask or has inserts in the nostrils so that air under pressure passes from the hose into the nostrils. The pressurized air passing into the nostrils causes an air stint that holds the soft palate and uvula up from the windpipe so that strangulation does not occur. However, CPAP machines: make disturbing low humming noises; the excess air introduced into the nose and mouth dry out the mouth and may cause choking; and for a person who is claustrophobic, the placement of the equipment over the face and nostrils may create a horrendous feeling of anxiety.

Thus, there has been a need to provide a means for preventing snoring and obstructive sleep apnea that is effective, inexpensive, easy to use, and overcomes many of the problems associated with treatments for snoring and obstructive sleep apnea used in the prior art.

SUMMARY OF THE INVENTION

The present invention is directed to an effective, inexpensive, efficient, easy to use, appliance for preventing snoring and obstructive sleep apnea. The appliance includes a headgear and a mouthpiece which function as a unit to provide the necessary relief from both snoring and obstructive sleep apnea. The headgear includes an adjustable headband that encircles the upper portion of a user's head at the forehead; an adjustable chin strap that passes over the crown of the head and under the chin of the user to maintain the user's mouth closed about the mouthpiece; a back strap that passes from the forehead over the crown of the head and down the user's back; retraining means secured to the rear end of the back strap that exerts a restraining force on the back strap and the upper portion of the headgear to keep the user's head from slouching forward; and an object, secured to the rear end of the back strap, that makes it uncomfortable for the user to lie on his/her back.

Preferably, the means for exerting a restraining force on the back strap to keep the user's head from slouching forward is a restraining belt that passes around the trunk or torso of the user. The restraining belt is adjustable in length to be comfortably fitted to user's torso. Preferably, the back strap is also adjustable in length to locate the restraining belt about the torso of the user in a desired location and to locate the object on the back of the user at a desired location. While other means can be used to make the lengths of the headband, the chin strap, the back strap and the restraining belt adjustable, it is preferred to use velcro or other similar means that enable the lengths of these headgear components to be quickly, easily and accurately adjusted to the required or desired length or size.

Preferably, the object for making it uncomfortable for the user to lie on his/her back is an object secured to the rear end of the back strap which is sufficiently thick and limited in size, such as a tennis ball, to apply localized pressure to the user's back when located intermediate the user's back and a firm surface. The object is preferably secured to the rear end of the back strap by containing the object in a pouch that is either directly secured to the back strap or indirectly secured to the back strap through the restraining belt.

The mouthpiece is flexible and includes a thin, flexible or resilient front sheet that extends across the front of the user's mouth between the upper and lower gums and in front of the user's teeth to prevent breathing through the mouth; and a thin, flexible or resilient back tab or flap that, in use, extends from an inner upper portion of the flexible front sheet to a location behind the user's lower front teeth to pull the user's lower jaw forward so that the uvula and soft palate can not fall over the windpipe.

The headgear and mouthpiece function as a unit to provide an appliance which is comfortable to wear and inhibits or prevents both snoring and obstructive sleep apnea. The chin strap of the headgear cooperates with the mouthpiece to assure that the mouth piece is not dislodged during sleep. The restraining belt, through the back strap, exerts a restraining force on the upper portion of the headgear to prevent the user's head from slouching forward. The positioning of a ball or similar object on the user's back further inhibits snoring or obstructive sleep apnea by preventing the user from sleeping on his/her back.

BRIEF DESCRIPTION OF THE DRAWINGS

FIG. 1 is a perspective view of the appliance headgear.

FIG. 2 is a side view of the appliance headgear in use.

FIG. 3 is a view of the headgear taken substantially along lines 3—3 of FIG. 2 and showing the attachment of the chin strap and the back strap to the headband of the headgear.

FIG. 4 is a detail of the under chin portion of the headgear chin strap in FIG. 1 that is designated by the reference numeral 4.

FIG. 5 is a detail of the circled portion of headband in FIG. 2 that is designated by the reference numeral 5.

FIG. 6 is a detail of the circled portion of the back strap in FIG. 2 that is designated by the reference numeral 6.

DESCRIPTION OF THE PREFERRED EMBODIMENTS

Figure 7:
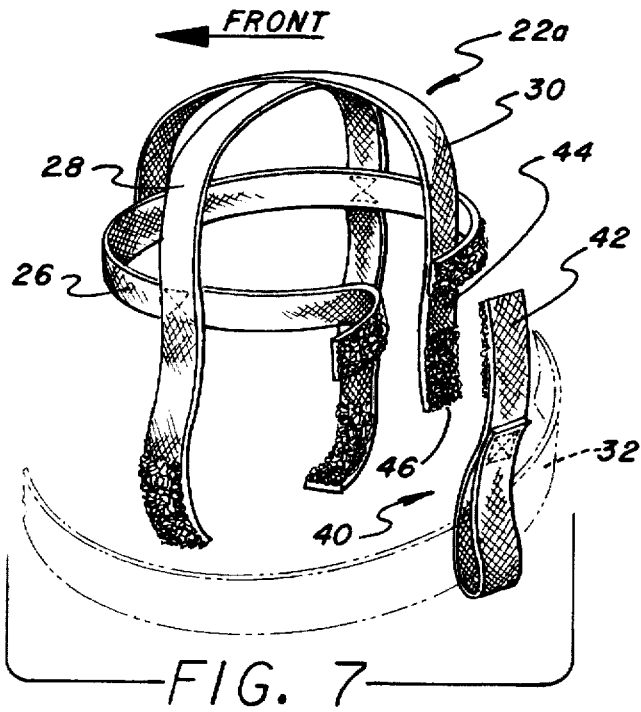
FIG. 7 is a perspective view of the headgear showing the back strap with a lower portion that is separably and adjustably attached to the upper portion.

The appliance 20 of the present invention includes a headgear 22 or 22a and a mouthpiece 24 which function as a unit to provide the necessary relief from both snoring and sleep apnea. FIGS. 1–12 show to two embodiments of the headgear 22 and 22a and FIGS. 13–16 show the mouthpiece 24.

The headgear 22 or 22a includes an adjustable headband 26 for encircling the upper portion of a user's head at the forehead; an adjustable chin strap 28 for passing over the crown of the head and under the chin of the user to maintain the user's mouth closed about the mouthpiece 24; a back strap 30 for passing from the forehead over the crown of the head and down the user's back; restraining means 32 secured to the rear end of the back strap for exerting a restraining force on the back strap and the upper portion of the headgear to keep the user's head from slouching forward; and an object 34 secured to the rear end of the back strap for making it uncomfortable for the user to lie on his/her back.

Preferably, the headband 26, the chin strap 28 and the back strap 30 are all made of an inextensible or inelastic, soft, flexible material, such as but not limited to a cloth material about 1/16th of an inch thick by about 1¼ inches wide. The headgear 22 or 22a is sized to fit heads of various sizes.

Preferably, both the headband 26 and the chin strap 28 have free ends 36 and 38 respectively that are provided with velcro (as shown in FIGS. 3–5), snap fasteners or similar means to permit the length or circumference of the headband 26 and the chin strap 28 to be easily and quickly adjusted to fit the head of a particular user and to be securely fastened, once adjusted, to maintain the headgear in place and the user's mouth closed about the mouthpiece 24 as shown in FIG. 2. As shown in FIGS. 1–3, the chin strap 28 is stitched, stapled or otherwise secured to the headband 26 along the side portions of the headband.

The forward end of the back strap 30 is stitched, stapled or otherwise secured to the forward portion of the headband 26 as 20 shown in FIGS. 1–3 and 7. The back strap 30 passes over the crown of the user's head and is again stitched, stapled or otherwise secured to the rear portion of the headband as shown in FIGS. 1–3 and 7. At the crown of the head the chin strap 28 and the back strap 30 are stitched, stapled or otherwise secured together as shown in FIGS. 1, 2 and 7.

As shown in FIGS. 1 and 7, the back strap 30 extends on down past the headband 26 to a location that is preferably, as shown in FIG. 2, between the shoulder blades of the user but may be located farther down the back if desired. Preferably, the free rear end of the back strap 30 is provided with a loop 40 that can be opened or closed by securing or detaching velcro fasteners as shown in FIGS. 1, 2, 6 and 7, snap fasteners or other similar fastener means. In the embodiment of the headgear 22, shown in FIGS. 1 and 2, the back strap 30 is made in one piece. In the embodiment of the headgear 22a, shown in FIG. 7, the back strap 30 is made in two pieces. The rear piece 42 of the back strap is detachably secured to the front piece 44 of the back strap by velcro fasteners 46, as shown in FIG. 7, snap fasteners or similar fastening means and can be of various lengths to locate the restraining means 32 at a desired location around the trunk or torso of the user. However, like the first embodiment, the length of the rear piece 42 of the back strap 30 is preferably such as to locate the free end of the back strap 30 between the shoulder blades of the user.

Figure 8:
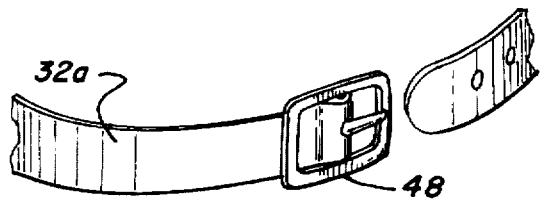
FIGS. 8–10 are partial perspective views of three types of restraining belts that can be used with the headgear of the present invention.
Figure 9:
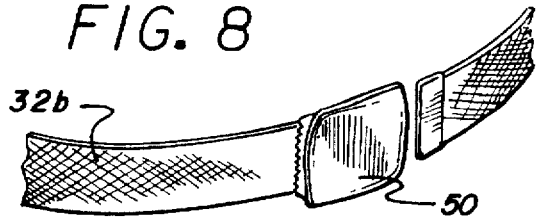
Figure 10:
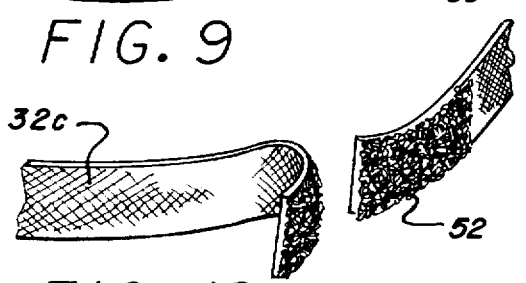

Preferably, the restraining means 32 for exerting a restraining force on the back strap 30 and the upper portion of the headgear to keep the user's head from slouching forward is a restraining belt of the type shown in FIGS. 8–10 that passes beneath the arms and around the trunk or torso of the user as shown in FIG. 2. As discussed above, preferably the restraining belt 32a, 32b or 32c passes immediately beneath the arms, around the chest and over the shoulder blades of the user. However, if desired, the restraining belt may extend around the trunk or torso of the user at a lower level. The restraining belt 32a, 32b or 32c is adjustable in length through the use of belt buckles 48 or 50 (as shown in FIGS. 8 and 9), velcro fasteners 52 (as shown in FIG. 10), or similar fastening means that can be quickly, easily and comfortably fitted to user's trunk or torso.

Preferably, the object 34 for making it uncomfortable for the user to lie on his/her back is an object, secured to the rear end of the back strap 30, which is sufficiently thick and limited in size, such as a tennis ball 34a, to apply localized pressure to the user's back when located intermediate the user's back and a firm surface. As discussed above, preferably, the back strap 30 is sized or adjusted in length to locate the restraining belt 32 about the trunk or torso of the user in a desired location and to locate the object 34 on the back of the user at a desired location, such as between the shoulder blades of the user.

Figure 11:
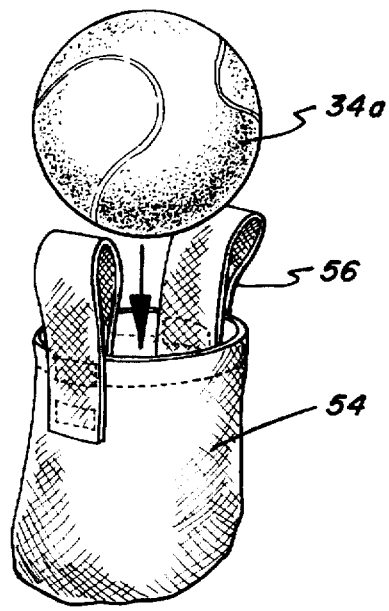
FIG. 11 is a perspective view of a pouch for holding a ball or a similar object and securing the ball or the similar object to the headgear.
Figure 12:
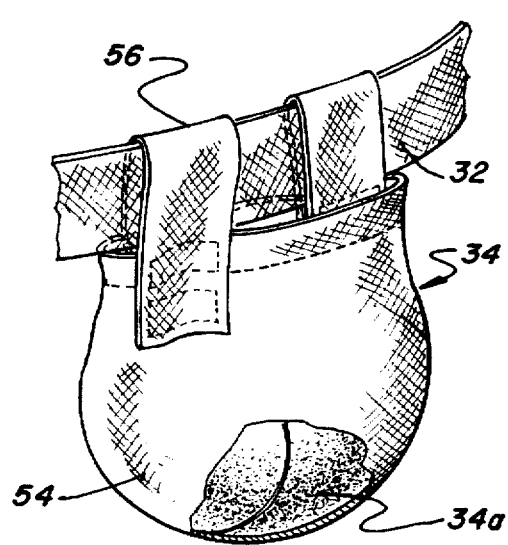
FIG. 12 is a perspective view of the pouch of FIG. 11 holding a ball and secured to the restraining belt of the headgear.
Figures 13, 14, 15, 16:
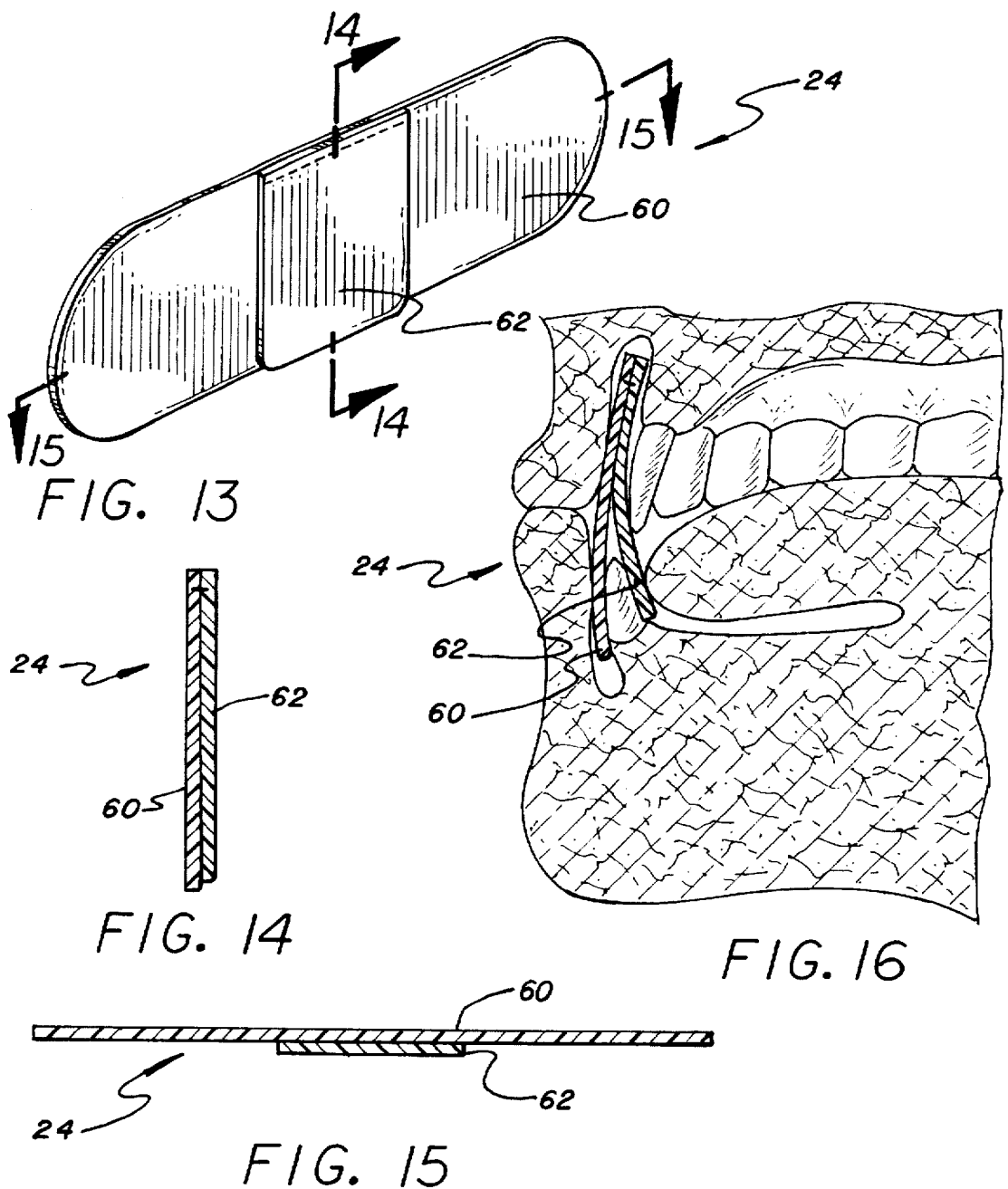
FIG. 13 is a perspective view of a mouthpiece of the present invention.
FIG. 14 is a vertical section of the mouthpiece taken substantially along lines 14—14 of FIG. 13.
FIG. 15 is a horizontal section of the mouthpiece taken substantially along lines 15—15 of FIG. 13.
FIG. 16 is a vertical section through the mouthpiece in place within a user's mouth.

The object 34 is preferably secured to the rear end of the back strap 30 by containing the object in a pouch 54 that is either directly secured to the back strap 30 by a snap fastener, button and button hole fastener, or similar fastening means, not shown, or indirectly secured to the back strap 30 through the restraining means or belt 32 by loops 56, as shown in FIGS. 11 and 12, or other fastening means. By locating the loops 56 of the pouch 54 on either side of the loop 40 of the back strap, the pouch and thus, the object, e.g. tennis ball 34a, can be maintained at a central location of the user's back during sleep.

As shown in FIGS. 13–16, the mouthpiece 24 is flexible and includes a thin, flexible or resilient front sheet 60 that extends across the front of the user's mouth between the upper and lower gums and in front of the user's teeth to prevent breathing through the mouth; and a thin, flexible or resilient back tab or flap 62 that, in use, extends from an inner upper portion of the flexible sheet 60 to a location behind the user's lower front teeth to pull the user's lower jaw forward so that the uvula and soft palate can not fall over the windpipe. The mouthpiece may be made of a thin, flexible or resilient, rubber material (e.g. silicone rubber); a thin, flexible or resilient, synthetic resin material; or any other thin, flexible or resilient, non-toxic material that will easily conform to the user's mouth and exert a forward force on the user's lower front teeth to pull the user's lower jaw forward. As shown in FIGS. 13–16, the upper end of the tab or flap 62 may be stitched to the upper portion of the front sheet 60. In addition, it is contemplated that the upper portion of the rear flap or tab 62 may be adhesively bonded, heat bonded, or otherwise secured to the upper portion of the front sheet 60 or that the front sheet 60 and the rear tab or flap 62 may be molded or otherwise formed in one piece.

In a preferred embodiment, the mouthpiece 24 is made of a thin silicone rubber about 1/32 of an inch thick. The front sheet 60 of the mouthpiece 24 is about 5 inches wide by about 1½ inches in height and the rear flap or tab of 62 of the mouthpiece 24 about 1¼ inches wide and extends from about 1¼ to about 1¾ of an inch in height so that it extends to or beyond the lower edge of the front sheet 60.

Thus, the headgear 22 or 22a and the mouthpiece 24 function as a unit to provide an appliance 20 which is comfortable to wear and inhibits or prevents both snoring and obstructive sleep apnea. The chin strap 28 of the headgear 22 keeps the user's mouth closed about the mouthpiece, as shown in FIG. 2, to assure that the mouthpiece 24 is not dislodged during sleep. The back strap 30 and the restraining means or belt 32 exert a restraining force on the upper portion of the headgear 22 to keep the user's head from slouching forward and cutting off the airway in the throat. In addition, the invention permits the positioning of a ball or similar object 34 on the user's back to prevent the user from sleeping on his back. Thus, the appliance 20 thereby further inhibits snoring and obstructive sleep apnea.

In describing the invention, certain embodiments have been used to illustrate the invention and the practices thereof. However, the invention is not limited to these specific embodiments as other embodiments and modifications within the spirit of the invention will readily occur to those skilled in the art on reading this specification. Thus, the invention is not intended to be limited to the specific embodiments disclosed, but is to be limited only by the claims appended hereto.

What is claimed is:

1. An appliance combination for preventing snoring and obstructive sleep apnea, comprising:

a headgear comprising a headband for encircling the upper portion of a user's head at the forehead; the headband being adjustable in circumferential length to be fitted to the head dimension of the user; a chin strap for passing over the crown of the head and under the chin of the user; the chin strap being secured to opposing side portions of the headband and being adjustable in circumferential length to be fitted to the head dimension of the user to maintain the user's mouth closed about a mouthpiece used in combination with the headgear; a back strap for passing from the forehead over the crown of the head and down the back of the user; a first end of the back strap being secured to a forward portion of the headband and a second end of the back strap extending below the headband at the rear of the user's head to the user's back; means secured to the second end of the back strap for exerting a restraining force on the back strap and an upper portion of the headgear to keep the user's head from slouching forward; and means secured to the second end of the back strap for making it uncomfortable for the user to lie on his/her back; and the mouthpiece being flexible and comprising a thin, flexible front sheet for extending across the front of the user's mouth between the upper and lower gums and in front of the user's teeth for preventing breathing through the mouth; and a thin, flexible back tab for extending from an inner upper portion of the flexible sheet to behind the user's lower front teeth for pulling the user's lower jaw forward.

2. The appliance combination according to claim 1, wherein: the means for making it uncomfortable for the user to lie on his/her back is an object secured to the second end of the back strap which is sufficiently thick to apply localized pressure to the user's back when located intermediate the user's back and a firm surface.

3. The appliance combination according to claim 2, wherein: the means for exerting a restraining force on the back strap to keep the user's head from slouching forward is a restraining belt for passing around the torso of the user; and the restraining belt being adjustable in length to be fitted to user's torso.

4. The appliance combination according to claim 3, wherein: the object is a ball is carried in a sack secured to the restraining belt.

5. The appliance combination according to claim 4, wherein: the back strap is adjustable in length to locate the restraining belt about the torso of the user in a desired location and to locate the ball on the back of the user at a desired location.

6. The appliance combination according to claim 5, wherein: the head band, the chin strap, the back strap, and the restraining belt all have hook and loop or hook and pile means for permitting quick and easy adjustments to their lengths.

7. The appliance combination according to claim 5, wherein: the flexible front sheet of the mouthpiece is about 5 inches wide, about 1½ inches high, and about 1/32 of an inch thick; and the back tab of the mouthpiece is about 1¼ inches wide, about 1¼ to about 1 ¾ inches in height, and about 1/32 of an inch thick.

8. The appliance combination according to claim 1, wherein: the means for exerting a restraining force on the back strap to keep the user's head from slouching forward is a restraining belt for passing around the torso of the user; and the restraining belt being adjustable in length to be fitted to user's torso.

9. The appliance combination according to claim 8, wherein: the back strap is adjustable in length to locate the restraining belt about the torso of the user in a desired location.

10. The appliance combination according to claim 9, wherein: the head band, the chin strap, the back strap, and the restraining belt all have hook and loop or hook and pile means for permitting quick and easy adjustments to their lengths.

11. The appliance combination according to claim 9, wherein: the flexible front sheet is about 5 inches wide, about 1½ inches high, and about 1/32 of an inch thick; and the back tab is about 1¼ inches wide, about 1¼ to about 1¾ inches in height, and about 1/32 of an inch thick.

12. The appliance combination according to claim 1, wherein: the flexible front sheet is about 5 inches wide, about 1½ inches high, and about 1/32 of an inch thick; and the back tab is about 1¼ inches wide, about 1¼ to about 1¾ inches in height, and about 1/32 of an inch thick.

13. An appliance combination for preventing snoring and obstructive sleep apnea, comprising:

a headgear comprising a headband for encircling the upper portion of a user's head at the forehead; the headband being adjustable in circumferential length to be fitted to the head dimension of the user; a chin strap for passing over the crown of the head and under the chin of the user; the chin strap being secured to opposing side portions of the headband and being adjustable in circumferential length to be fitted to the head dimension of the user to maintain the user's mouth closed about a mouthpiece used in combination with the headgear; a back strap for passing from the forehead over the crown of the head and down the back of the user; a first end of the back strap being secured to a forward portion of the headband and a second end of the back strap extending below the headband at the rear of the user's head to the user's back; and means secured to the second end of the back strap for exerting a restraining force on the back strap and an upper portion of the headgear to keep the user's head from slouching forward; and the mouthpiece being flexible and comprising a thin, flexible front sheet for extending across the front of the user's mouth between the upper and lower gums and in front of the user's teeth for preventing breathing through the mouth; and a thin, flexible back tab for extending from an inner upper portion of the flexible sheet to behind the user's lower front teeth for pulling the user's lower jaw forward.

14. The appliance combination according to claim 13, wherein: the means for exerting a restraining force on the back strap to keep the user's head from slouching forward is a restraining belt for passing around the torso of the user; and the restraining belt being adjustable in length to be fitted to user's torso.

* * * * *